(12) United States Patent
Hyde et al.

(10) Patent No.: US 9,337,659 B2
(45) Date of Patent: *May 10, 2016

(54) SYSTEMS CONFIGURED TO TRANSMIT OPTICAL POWER SIGNALS TRANSDERMALLY OUT OF A LIVING SUBJECT, AND DEVICES AND METHODS

(71) Applicant: SEARETE LLC, Bellevue, WA (US)

(72) Inventors: Roderick A. Hyde, Redmond, WA (US); Muriel Y. Ishikawa, Livermore, CA (US); Dennis J. Rivet, Chesapeake, VA (US); Elizabeth A. Sweeney, Seattle, WA (US); Lowell L. Wood, Jr., Bellevue, WA (US); Victoria Y. H. Wood, Livermore, CA (US)

(73) Assignee: GEARBOX, LLC, Bellevue, WA (US)

( * ) Notice: Subject to any disclaimer, the term of this patent is extended or adjusted under 35 U.S.C. 154(b) by 446 days.

This patent is subject to a terminal disclaimer.

(21) Appl. No.: 13/710,158

(22) Filed: Dec. 10, 2012

(65) Prior Publication Data

US 2013/0103117 A1    Apr. 25, 2013

Related U.S. Application Data

(62) Division of application No. 12/283,911, filed on Sep. 15, 2008, now Pat. No. 8,340,777.

(51) Int. Cl.
*A61N 1/37* (2006.01)
*H02J 4/00* (2006.01)
*A61N 1/378* (2006.01)
(Continued)

(52) U.S. Cl.
CPC ............... *H02J 4/00* (2013.01); *A61N 1/3785* (2013.01); *A61N 1/37217* (2013.01); *A61N 1/37223* (2013.01); *H02J 17/00* (2013.01); *H04B 10/1141* (2013.01); *H04B 13/005* (2013.01)

(58) Field of Classification Search
CPC . A61N 1/378; A61N 1/3787; A61N 1/37217; A61N 1/3785; A61N 1/37211
See application file for complete search history.

(56) References Cited

U.S. PATENT DOCUMENTS 5,320,098 A    6/1994 Davidson
5,387,529 A    2/1995 Davidson
(Continued)

OTHER PUBLICATIONS

U.S. Appl. No. 13/604,005, filed Sep. 5, 2012, Hyde et al.
(Continued)

*Primary Examiner* — Eric D. Bertram
(74) *Attorney, Agent, or Firm* — Dorsey & Whitney LLP (57) ABSTRACT

In an embodiment, a system includes an internal optical power transmitter configured to be disposed within a living subject. The internal optical power transmitter includes a power source configured to provide electrical energy and an electrical-optical converter operably coupled to the power source. The electrical-optical converter may be configured to convert at least a portion of the electrical energy into one or more optical power signals transdermally transmittable out of the living subject. The system further includes an external optical-electrical converter configured to convert the one or more optical power signals into one or more electrical power signals and at least one external device configured to be operably coupled to the external optical-electrical converter and powered by the one or more electrical power signals. Embodiments of methods, biocompatible electrical-optical converters, and internal optical power transmitters are also disclosed.

26 Claims, 6 Drawing Sheets

(51) Int. Cl.
  *A61N 1/372* (2006.01)
  *H02J 17/00* (2006.01)
  *H04B 10/114* (2013.01)
  *H04B 13/00* (2006.01)

(56) References Cited

U.S. PATENT DOCUMENTS

| | | | |
|---|---|---|---|
| 5,835,457 A | 11/1998 | Nakajima | |
| 5,889,735 A | 3/1999 | Kawata et al. | |
| 5,897,330 A | 4/1999 | Watanabe et al. | |
| 6,409,674 B1 | 6/2002 | Brockway et al. | |
| 6,898,464 B2 | 5/2005 | Edell et al. | |
| 8,280,520 B2 | 10/2012 | Hyde et al. | |
| 8,295,941 B2 | 10/2012 | Hyde et al. | |
| 2006/0139000 A1 | 6/2006 | Bailey et al. | |
| 2006/0183965 A1 | 8/2006 | Kasic, II et al. | |
| 2007/0027505 A1 | 2/2007 | Ginggen | |
| 2007/0167758 A1 | 7/2007 | Costello | |
| 2007/0255223 A1 | 11/2007 | Phillips et al. | |
| 2008/0097545 A1 | 4/2008 | Propato | |
| 2009/0068620 A1 | 3/2009 | Knobel et al. | |
| 2009/0171404 A1* | 7/2009 | Irani et al. | 607/2 |
| 2010/0065097 A1 | 3/2010 | Hyde et al. | |
| 2010/0067920 A1 | 3/2010 | Hyde et al. | |
| 2010/0070003 A1 | 3/2010 | Hyde et al. | |
| 2010/0272299 A1* | 10/2010 | Van Schuylenbergh et al. | 381/315 |
| 2010/0295372 A1 | 11/2010 | Hyde et al. | |
| 2013/0103117 A1 | 4/2013 | Hyde et al. | |

OTHER PUBLICATIONS

U.S. Appl. No. 13/603,904, filed Sep. 5, 2012, Hyde et al.
U.S. Appl. No. 13/603,859, filed Sep. 5, 2012, Hyde et al.
U.S. Appl. No. 13/626,715, filed Sep. 25, 2012, Hyde et al.
U.S. Appl. No. 13/627,331, filed Sep. 26, 2012, Hyde et al.
U.S. Appl. No. 13/627,391, filed Sep. 26, 2012, Hyde et al.
U.S. Appl. No. 13/627,442, filed Sep. 26, 2012, Hyde et al.

* cited by examiner

SYSTEMS CONFIGURED TO TRANSMIT OPTICAL POWER SIGNALS TRANSDERMALLY OUT OF A LIVING SUBJECT, AND DEVICES AND METHODS

CROSS-REFERENCE TO RELATED APPLICATIONS

For purposes of the USPTO extra-statutory requirements, the present application constitutes a divisional of U.S. patent application Ser. No. 12/283,911 filed on 15 Sep. 2008, now U.S. Pat. No. 8,340,777 issued on 25 Dec. 2012, entitled SYSTEMS CONFIGURED TO TRANSMIT OPTICAL POWER SIGNALS TRANSDERMALLY OUT OF A LIVING SUBJECT, AND DEVICES AND METHODS, naming Roderick A. Hyde, Muriel Y. Ishikawa, Dennis J. Rivet, Elizabeth A. Sweeney, Lowell L. Wood, Jr., and Victoria Y. H. Wood, as inventors.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an embodiment, a system includes an internal optical power transmitter configured to be disposed within a living subject. The internal optical power transmitter includes a power source configured to provide electrical energy and an electrical-optical converter operably coupled to the power source. The electrical-optical converter may be configured to convert at least a portion of the electrical energy into one or more optical power signals transdermally transmittable out of the living subject and having a power of at least about 10 µW.

In an embodiment, a system includes an internal optical power transmitter configured to be disposed within a living subject. The internal optical power transmitter includes a power source configured to provide electrical energy and an electrical-optical converter operably coupled to the power source. The electrical-optical converter may be configured to convert at least a portion of the electrical energy into one or more optical power signals transdermally transmittable out of the living subject. The system further includes an external optical-electrical converter configured to convert the one or more optical power signals into one or more electrical power signals, and at least one external device configured to be operably coupled to the external optical-electrical converter and powered by the one or more electrical power signals.

In an embodiment, a method includes converting electrical energy within a living subject into one or more optical power signals. The method further includes transmitting the one or more optical power signals transdermally out of the living subject with a power of at least about 10 µW.

In an embodiment, a method includes converting electrical energy within a living subject into one or more optical power signals, and modifying one or more optical parameters of the one or more optical power signals. The method further includes transmitting the one or more optical power signals transdermally out of the living subject after the modifying.

In an embodiment, a method includes receiving one or more optical power signals transmitted transdermally out of a living subject and converting the one or more optical signals to one or more electrical power signals. The method further includes powering at least one device located externally to the living subject using the one or more electrical power signals.

In an embodiment, an internal optical power transmitter configured to be disposed within a living subject includes a power source configured to provide electrical energy and an electrical-optical converter operably coupled to the power source. The electrical-optical converter may be configured to convert at least a portion of the electrical energy into one or more optical power signals transdermally transmittable out of the living subject and having a power of at least about 10 µW. The internal optical power transmitter includes a biocompatible protective packaging enclosing the power source and the electrical-optical converter.

In an embodiment, an internal optical power transmitter configured to be disposed within a living subject includes a power source configured to provide electrical energy and an electrical-optical converter operably coupled to the power source. The electrical-optical converter may be configured to convert at least a portion of the electrical energy into one or more optical power signals transdermally transmittable out of the living subject. The internal optical power transmitter further includes one or more optical elements configured to interact with the one or more optical power signals prior to transmission out of the living subject. A biocompatible protective packaging encloses the power source, electrical-optical converter, and beam steering device.

In an embodiment, an internal optical power transmitter configured to be disposed within a living subject includes a power source configured to provide electrical energy. The internal optical power transmitter further includes an electrical-optical converter operably coupled to the power source. The electrical-optical converter may be configured to convert at least a portion of the electrical energy into one or more optical power signals transdermally transmittable out of the living subject. The internal optical power transmitter also includes one or more optical components configured to interact with the one or more optical power signals prior to transmission out of the living subject. A biocompatible protective packaging encloses the power source, electrical-optical converter, and one or more optical elements.

In an embodiment, an internal optical power transmitter configured to be disposed within a living subject includes a power source configured to provide electrical energy, an energy storage device coupled to the power source and configured to store the electrical energy, and an electrical-optical converter operably coupled to the energy storage device. The electrical-optical converter is configured to convert at least a portion of the electrical energy into one or more optical power signals transdermally transmittable out of the living subject. A biocompatible protective packaging encloses the power source, the energy storage device, and the electrical-optical converter.

In an embodiment, a biocompatible electrical-optical converter includes at least one light-emitting device. The at least one light-emitting device may be configured to convert at least a portion of electricity to one or more optical power signals that are transdermally transmittable through tissue of a living subject, and output the one or more optical power signals with a power of at least about 10 µW. The biocompatible electrical-optical converter further includes a biocompatible protective packaging that encloses the at least one light-emitting device and is transmissive to the one or more optical power signals.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other subject matter described herein will become apparent after reading the teachings set forth herein.

DETAILED DESCRIPTION

Embodiments disclosed herein are directed to systems configured to transmit one or more optical power signals transdermally out of a living subject to power at least one external device, internal optical power transmitters for use in such systems, biocompatible electrical-optical converters for use in such systems or internal optical power transmitters, and methods of use. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein.

Figure 1:
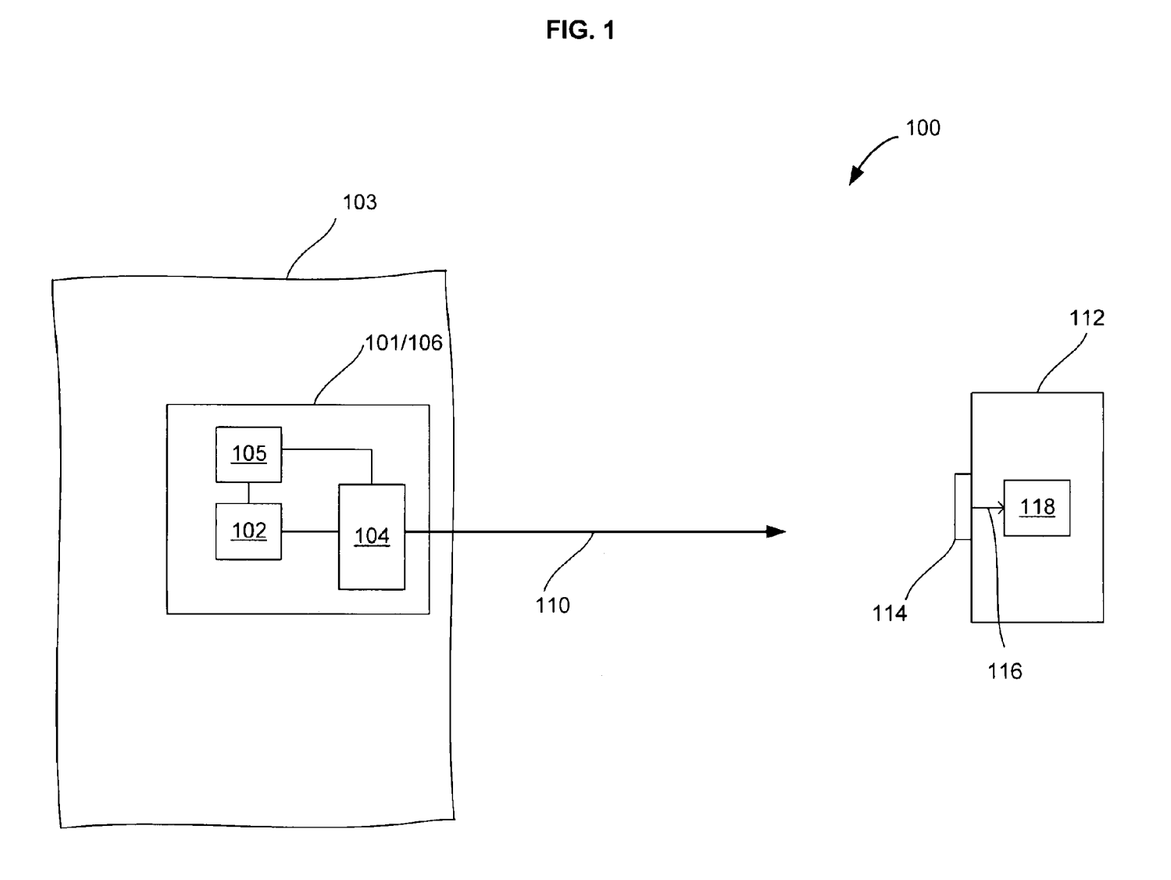
FIG. 1 is a functional block diagram of an embodiment of a system configured to transmit one or more optical power signals transdermally out of a living subject to power at least one external device.

FIG. 1 is a functional block diagram of an embodiment of a system 100 configured to transmit one or more optical power signals transdermally out of a living subject to power at least one external device. The system 100 includes an internal optical power transmitter 101 configured to be disposed within a living subject 103, such as being embedded in tissue, muscle, or bone of a human being. The internal optical power transmitter 101 includes a power source 102, an electrical-optical converter 104 operably coupled to the power source 102 to receive electricity (e.g., one or more electrical signals) therefrom, and control circuitry 105 configured to control distribution of electricity from the power source 102 to the electrical-optical converter 104 and the operation of the electrical-optical converter 104. The power source 102, electrical-optical converter 104, and control circuitry 105 may be configured to be disposed in a living subject 103, such as by being sized for being disposed in the living subject 103 or being biocompatible with the living subject 103. For example, the power source 102, electrical-optical converter 104, and control circuitry 105 may be compactly enclosed in a biocompatible protective packaging 106 that is disposed within the living subject 103 to form the internal optical power transmitter 101. In an embodiment, the power source 102, electrical-optical converter 104, and control circuitry 105 may each be individually enclosed in separate biocompatible protective packaging sections. The electrical-optical converter 104 is configured to convert at least a portion of the electricity received from the power source 102 into one or more optical power signals 110 that are transmittable through and out of tissue of the living subject 103 and have a power of at least about 10 µW.

The system 100 further includes at least one external device 112 positioned or positionable externally to the living subject 103 to receive the one or more optical power signals 110 transmitted out of the living subject 103. The at least one external device 112 includes an optical-electrical converter 114 (e.g., one or more photodiodes) configured to convert the received one or more optical power signals 110 into one or more electrical power signals 116. For example, the optical-electrical converter 114 may be integrated with or separate from the at least one external device 112. In some embodiments, the optical-electrical converter 114 may be associated with a receiving aperture (e.g., one or more collimation lenses, one or more reflectors, or other focusing optics) that direct the one or more optical power signals 110 to the underlying optical-electrical converter 114 or focus the one or more optical power signals 110 so that substantially all of the optical power is received by the optical-electrical converter 114. The at least one external device 112 further includes control circuitry 118 operably coupled to the optical-electrical converter 114 and configured to control the operation of the at least one external device 112 responsive to receiving the converted one or more electrical power signals 116.

In operation, electrical energy within the living subject 103 is converted into the one or more optical power signals 110, which are transmitted out of the living subject 103 with, for example, a power of at least about 10 µW. More specifically, the electrical-optical converter 104 transmits the one or more optical power signals 110 transdermally through and out of the living subject 103 responsive to instructions from the control circuitry 105, which are received by the optical-electrical converter 114 of the at least one external device 112. For example, the control circuitry 105 may be pre-programmed to direct the electrical-optical converter 104 to output the one or more optical power signals 110 at specific times throughout the day. The one or more optical power signals 110 are received by the optical-electrical converter 114, which converts the one or more optical power signals 110 to one or more electrical power signals 116. The one or more electrical power signals 116 may be used to power the at least one external device. For example, the control circuitry 118 receives the one or more electrical power signals 116 and uses the one or more electrical power signals 116 to power and control the operation of the at least one external device 112.

In an embodiment, the optical-electrical converter 114 of the at least one external device 112 may be placed in proximity to the electrical-optical converter 104 and abut tissue of the living subject 103. In an embodiment, the power of the one or more optical power signals 110 may be sufficient so that the at least one external device 112 may be positioned remote from the living subject 103 and the optical-electrical converter 104 therein.

The electrical-optical converter 104 may receive power from a variety of different types of power sources. According to various embodiments, the power source 102 may include an energy storage device, such as a battery or a capacitive device. In an embodiment, the power source 102 may include an electricity generator configured to convert internal body energy of the living subject 103 to electrical energy. For example, the electricity generator may include at least one of a fluid-flow generator configured to convert internal body fluid motion into electricity, a fluid-pressure generator configured to convert internal fluid pressure into electricity, a muscle-motion generator configured to convert internal muscle motion into electricity, an acceleration-motion generator configured to convert acceleration of the living subject 103 into electricity, or a thermal-electric generator configured to convert internal body heat into electricity. The power source 102 may include an energy storage device (e.g., a battery or capacitive device) coupled to a separate power source (e.g, any of the aforementioned electricity generator) and configured to store electrical energy generated by the separate power source. In such an embodiment, the control circuitry 118 may be operably coupled to the energy storage device and control distribution of the electricity therefrom to the electrical-optical converter 104. In some embodiment, the energy storage device and separate power source may be separately packaged in a biocompatible packaging.

The electrical-optical converter 104 may include at least one light-emitting device. For example, in some embodiments, the at least one light-emitting device of the electrical-optical converter 104 may include a light-emitting diode or a laser diode configured to transmit the converted electricity received from the power source 102 as the one or more optical power signals 110 with a power of at least about 10 µW. In more specific embodiments, the power output by the electrical-optical converter 104 may range from about 10 µW to about 10 W, about 10 µW to about 1 mW, about 1 mW to about 100 W, and about 100 mW to about 1 W. The electrical-optical converter 104 may output the one or more optical power signals 110 at a selected one or more wavelengths that are transmittable through tissue of the living subject 103. For example, the selected one or more wavelengths may include one or more infrared wavelengths having a wavelength of about 800 nm to about 1 mm. The selected one or more wavelengths may include one or more visible wavelengths having a wavelength of about 380 nm to about 750 nm.

As previously discussed, the power source 102 and components thereof, and electrical-optical converter 104 may be enclosed in the biocompatible protective packaging 106 that is at least partially transparent to the one or more optical power signals 110 output by the electrical-optical converter 104. The biocompatible protective packaging 106 may be formed from a number of different biocompatible polymeric materials, such as at least one of polyxylene, polyethylene, poly(ethylene oxide), polyurethane, or poly(butylene terephthalate). The biocompatible protective packaging 106 may also be formed from a number of different biocompatible ceramics, such as silicate-based ceramics. In some embodiments, the biocompatible protective packaging 106 may be in the form of a biocompatible coating made from at least one of the aforementioned biocompatible polymeric or ceramic materials and formed over a relatively less biocompatible housing that provides structural support for the biocompatible coating or a housing formed from at least one of the aforementioned biocompatible materials.

The control circuitry 105 may be configured to direct the electrical-optical converter 104 to output the one or more optical power signals 110 with one or more selected optical parameters. For example, the one or more selected optical parameters may include wavelength, start time, duration, end time, power, or time-integrated power of the one or more optical power signals 110.

The one or more optical power signals 110 may be employed to power a number of different external devices without limitation. For example, the at least one external device 112 may include a personal electronic device, such as a cell phone, personal data assistant, a video game device, or an electronic medical device.

Figure 2:
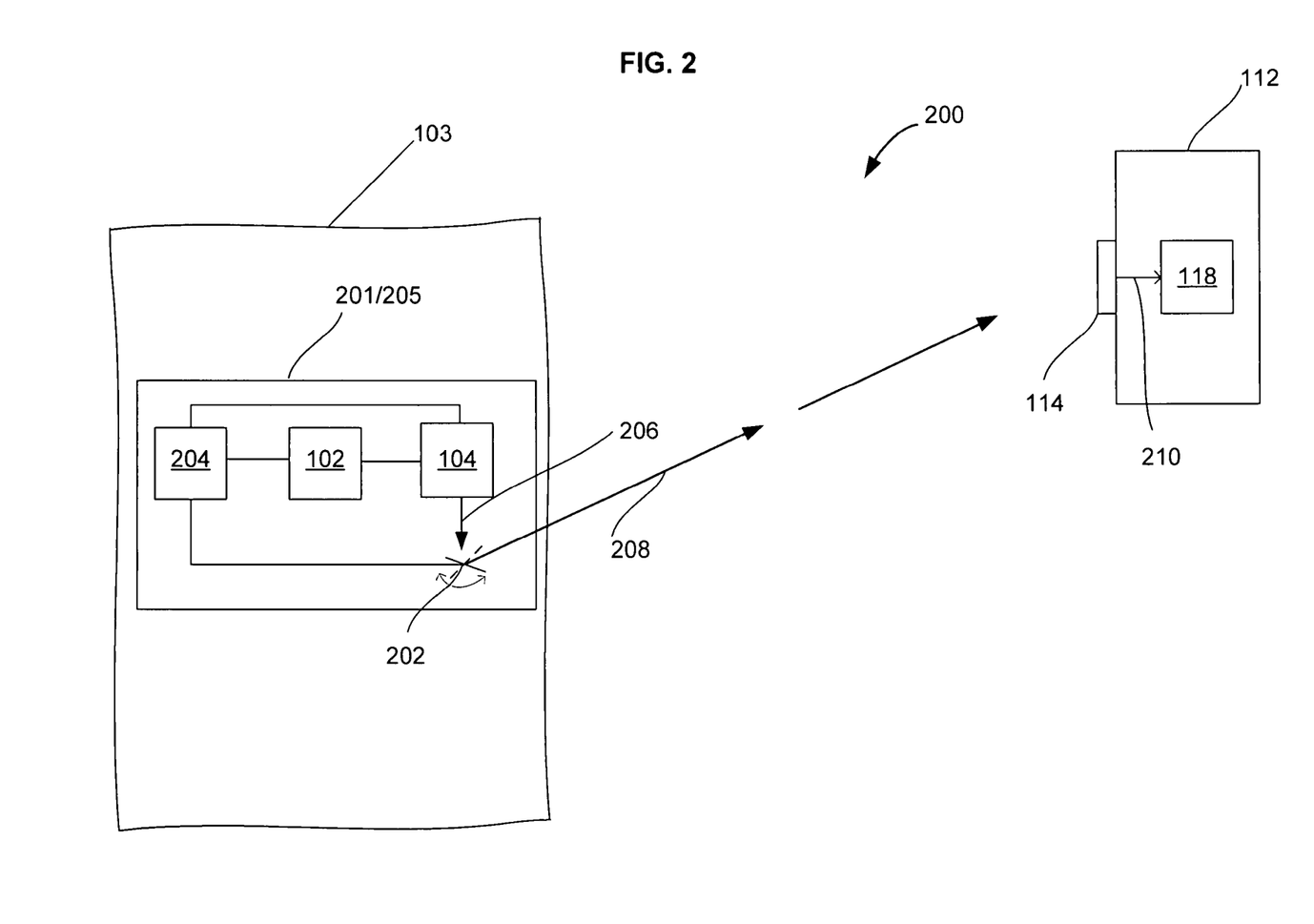
FIG. 2 is a functional block diagram of an embodiment of a system configured to transmit and selectively steer one or more optical power signals transdermally out of a living subject to power at least one external device.

FIG. 2 is a functional block diagram of an embodiment of a system 200 configured to transmit and selectively steer one or more optical power signals transdermally out of a living subject to power at least one external device. The system 200 includes an internal optical power transmitter 201 configured to be disposed within the living subject 103. The internal optical power transmitter 201 includes the power source 102, electrical-optical converter 104 operably coupled to the power source 102 to receive electricity therefrom, a beam steering device 202 in optical communication with the electrical-optical converter 104, and control circuitry 204 configured to control distribution of electricity from the power source 102 to the electrical-optical converter 104 and beam steering device 202 and control the operation of the electrical-optical converter 104 and beam steering device 202. The power source 102, electrical-optical converter 104, beam steering device 202, and control circuitry 204 may be enclosed individually or collectively in a biocompatible protective packaging 205 that is disposed within the living subject 103 and configured the same or similarly as the biocompatible protective packaging 108 (FIG. 1). The electrical-optical converter 104 is configured to convert at least a portion of the electricity received from the power source 102 into one or more optical power signals 206 that are transmittable through and out of tissue of the living subject 103 and have a power of at least about 10 µW or any of the power ranges previously described with respect to FIG. 1.

The beam steering device 202 is positioned to receive the one or more optical power signals 206 from the electrical-optical converter 104 and configured to selectively steer the one or more optical power signals 206 as one or more steered optical power signals 208 that are transmitted transdermally through tissue of and out of the living subject 103. According to various embodiments, the beam steering device 202 may include at least one of a diffraction grating, a micro-electro-mechanical scanner, an acoustic-optical device, or an electro-optical device configured to selectively steering the one or more optical power signals 206 as the one or more steered optical power signals 208. In an embodiment, the beam steering device 202 may be configured as a steerable mount that supports the electrical-optical converter 104 so that the one or more optical power signals 110 may be selectively steered or supports one or more optical elements. For example, the steerable mount may support one or more reflective elements (e.g., a spherical mirror) that receives the one or more optical power signals 206 and reflects them in a selected direction.

The control circuitry 204 operably coupled to the beam steering device 202 may be configured to direct the electrical-optical converter 104 to output the one or more optical power signals 208 with one or more selected optical parameters. For example, the one or more selected optical parameters may include wavelength, start time, duration, end time, power, or time-integrated power of the one or more steered optical power signals 208. The control circuitry 204 may also be configured to control a direction of the one or more optical power signals 208 that the beam steering device 202 steers the one or more optical power signals 206.

As with the system 100 shown in FIG. 1, the system 200 further includes at least one external device 112 positioned or positionable externally to the living subject 103 to receive the one or more steered optical power signals 208 transmitted out of the living subject 103 by the beam steering device 202.

In operation, the electrical-optical converter 104 transmits the one or more optical power signals 206 to the beam steering device 202 responsive to instructions from the control circuitry 204, which selectively steers the one or more optical power signals 206 (represented as the one or more steered optical power signals 208) prior to transmission out of the living subject 103. The one or more steered optical power signals 208 are received by the optical-electrical converter 114 of the at least one external device 112. The optical-electrical converter 114 converts the one or more steered optical power signals 208 to one or more electrical power signals 210. The control circuitry 118 receives the one or more electrical power signals 210 and uses the one or more electrical power signals 210 to power and control the operation of the at least one external device 112.

Figure 3:
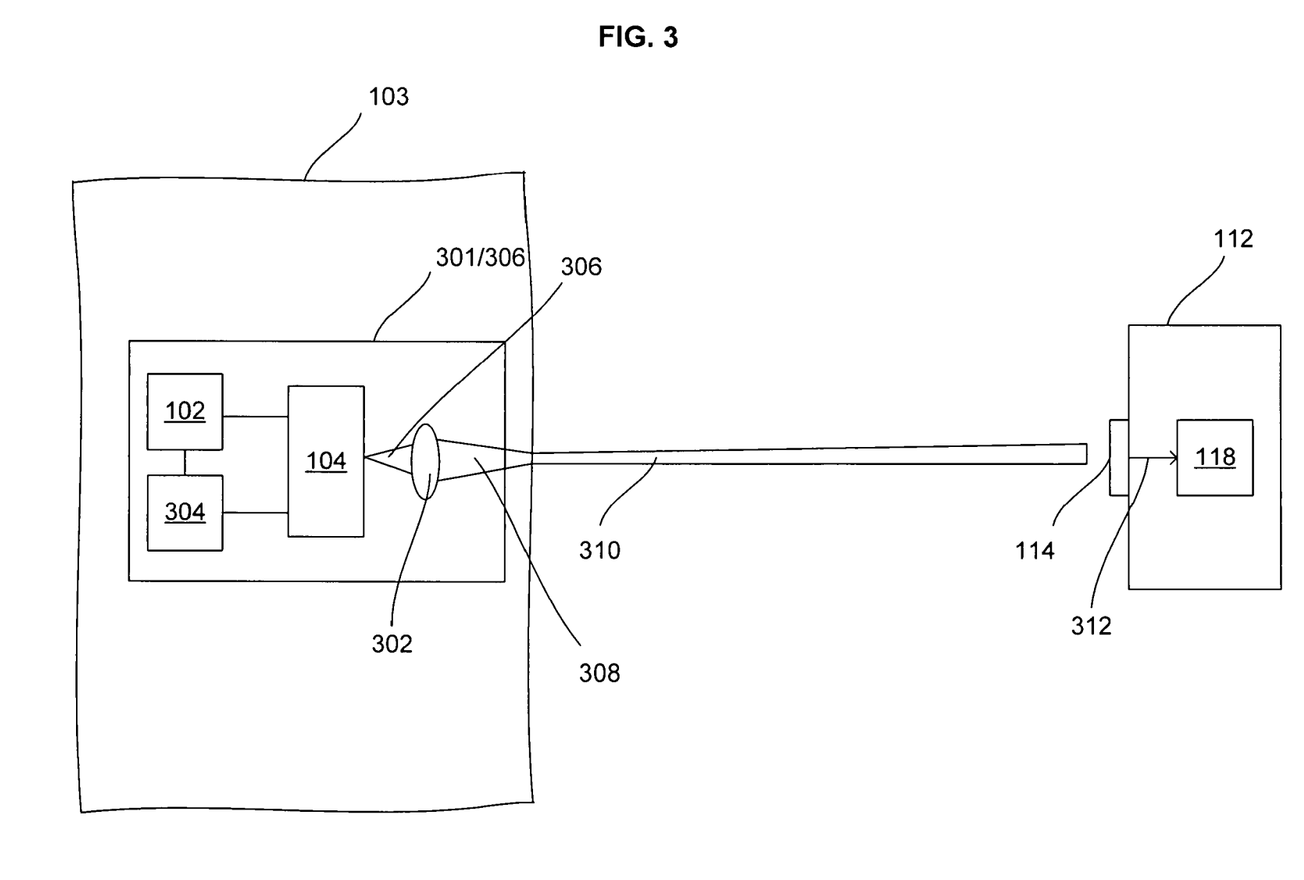
FIG. 3 is a functional block diagram of an embodiment of a system configured to focus one or more optical power signals prior to transmission transdermally out of a living subject to power at least one external device.

FIG. 3 is a functional block diagram of an embodiment of a system 300 configured to focus one or more optical power signals prior to transmission transdermally out of a living subject to power at least one external device to reduce optical spreading due to transmission through tissue of the living subject. The system 300 includes an internal optical power transmitter 301 configured to be disposed within the living subject 103. The internal optical power transmitter 301 includes the power source 102, electrical-optical converter 104 operably coupled to the power source 102 to receive electricity therefrom, focusing optics 302 in optical communication with the electrical-optical converter 104, and control circuitry 304 configured to control distribution of electricity from the power source 102 to the electrical-optical converter 104 and control the operation of the electrical-optical converter 104. The power source 102, electrical-optical converter 104, focusing optics 302, and control circuitry 304 may be enclosed individually or collectively in a biocompatible protective packaging 306 that is disposed within the living subject 103 and configured as the biocompatible protective packaging 106 (FIG. 1).

The electrical-optical converter 104 is configured to convert at least a portion of the electricity received from the power source 102 into one or more optical power signals 306 that are transmittable through and out of tissue of the living subject 103 and have a power of at least about 10 µW or any of the power ranges previously described with respect to FIG. 1. The focusing optics 302 are positioned to receive the one or more optical power signals 306 from the electrical-optical converter 104 and configured to focus the one or more optical power signals 306 to a selected angular spread, which are represented as one or more focused optical power signals 308 and transmitted transdermally through tissue of and out of the living subject 103 as the one or more optical power signals 310. For example, the focusing optics 302 may be configured to reduce a diameter or a divergence angle of a beam of the one or more optical signals 110. According to various embodiments, the focusing optics 302 may be configured as one or more lenses (e.g., one or more diffractive lenses or refractive lenses) or a reflective element (e.g., a spherical mirror or other type of mirror having optical power). By focusing the one or more optical power signals 306, the effect of optical spreading (e.g., scattering, diffraction, or refraction) as the light output by the electrical-optical converter 104 propagates through tissue of the living subject 103 may be at least partially countered. For example, in an embodiment, the focusing optics 302 may be configured to focus the one or more optical power signals 306 so that a beam diameter of the one or more optical power signals 310 transmitted transdermally out of the living subject 103 is about equal to a beam diameter output by the electrical-optical converter 104 prior to transmission through the tissue of the living subject 103.

As with the system 100 shown in FIG. 1, the system 300 further includes at least one external device 112 positioned or positionable externally to the living subject 103 to receive the one or more optical power signals 310 transmitted out of the living subject 103 by the beam steering device 202.

In operation, the electrical-optical converter 104 transmits the one or more optical power signals 306 to the focusing optics 302 responsive to instructions from the control circuitry 304, which focuses the one or more optical power signals 306 represented as the one or more focused optical power signals 308. The one or more focused optical power signals 308 are transmitted through the tissue of the living subject 103 and output as the one or more optical power signals 310 that are received by the optical-electrical converter 114 of the at least one external device 112. The optical-electrical converter 114 converters the one or more optical power signals 310 to one or more electrical power signals 312. The control circuitry 118 receives the one or more electrical power signals 312 and uses the one or more electrical power signals 312 to power and control the operation of the at least one external device 112.

In some embodiments, the internal optical power transmitter 301 may include a beam steering device (e.g., the beam steering device 202) configured to steer the one or more optical power signals 306 prior to focusing by the focusing optics 302. In other embodiments, the beam steering device may steer the one or more focused optical power signals 308.

Figure 4:
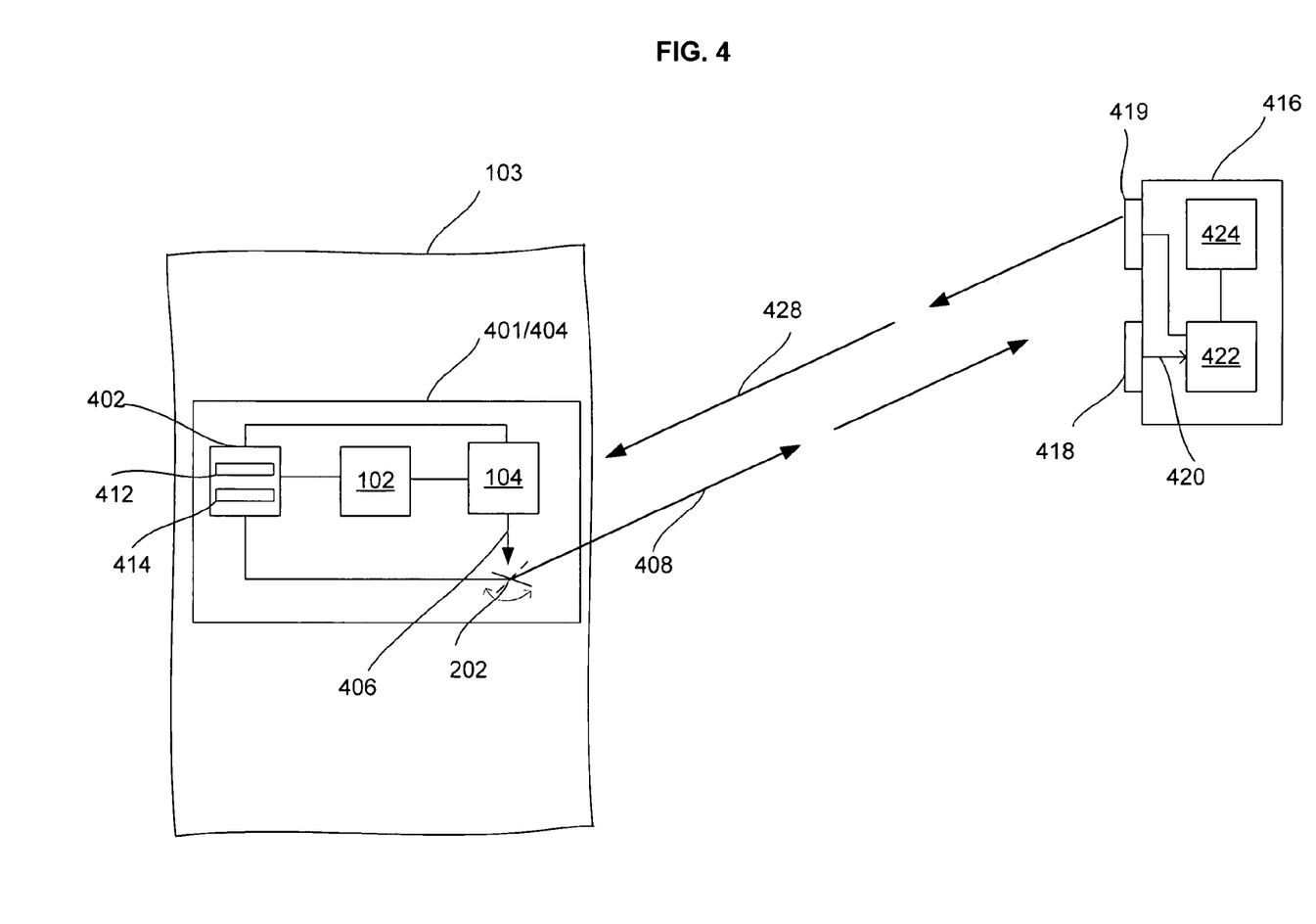
FIG. 4 is a functional block diagram of an embodiment of a system configured to transmit one or more optical power signals transdermally out of a living subject to power at least one external device responsive to receiving instructions from at least one external device.

FIG. 4 is a functional block diagram of an embodiment of a system 400 configured to transmit one or more optical power signals transdermally out of a living subject to power at least one external device responsive to receiving instructions from the at least one external device. The system 400 includes an internal optical power transmitter 401 configured to be disposed within the living subject 103. The internal optical power transmitter 401 includes the power source 102, electrical-optical converter 104 operably coupled to the power source 102 to receive electricity therefrom, beam steering device 202 in optical communication with the electrical-optical converter 104, and a controller 402 configured to control distribution of electricity from the power source 102 to the electrical-optical converter 104 and beam steering device 202 and control the operation of the electrical-optical converter 104 and beam steering device 202. The power source 102, electrical-optical converter 104, and controller 402 may be enclosed individually or collectively in a biocompatible protective packaging 404 that is disposed within the living subject 103 and configured the same or similarly as the biocompatible protective packaging 106 (FIG. 1). The electrical-optical converter 104 is configured to convert at least a portion of the electricity received from the power source 102 into one or more optical power signals 406 that are transmittable through and out of tissue of the living subject 103 and have a power of at least about 10 µW or any of the power ranges previously described with respect to FIG. 1. The beam steering device 202 is configured to selectively steer the one or more optical power signals 406 as one or more steered optical power signals 408 that are transmitted transdermally through tissue of and out of the living subject 103. The controller 402 includes control circuitry 412 coupled to a receiver 414 configured to receive control signals through the living subject 103.

The system 400 further includes at least one external device 416 (e.g., a cell phone, personal data assistant, a video game device, or an electronic medical device) positioned or positionable externally to the living subject 103 to receive the one or more steered optical power signals 408 transmitted out of the living subject 103 by the beam steering device 202. The at least one external device 416 includes an optical-electrical converter 418 configured to convert the received one or more steered optical power signals 408 into one or more electrical power signals 420. The at least one external device 416 further includes a transmitter 419 configured to transmit one or more optical control signals 428 encoding operational instructions for the internal optical power transmitter 401 that are transmittable transdermally through the living subject 103, and control circuitry 422 that is operably coupled to the optical-electrical converter 114 and transmitter 419. The control circuitry 422 is configured to control the operation of the transmitter 419, and the operation of the at least one external device 416 responsive to receiving the converted one or more electrical power signals 420 via the optical-electrical converter 418. The at least one external device 416 may also include a user interface 424 (e.g., a touch screen, keypad, or other suitable user interface) operably coupled to the control circuitry 422 to allow a user to direct the selective output of the one or more optical control signals 428 from the transmitter 419.

In operation, the user may direct, through the user interface 424, the transmitter 419 to selectively output the one or more optical control signals 428 that are received by the receiver 414 of the controller 402. Responsive to receiving the one or more optical control signals 428, the controller 402 directs the electrical-optical converter 104 to output the one or more optical power signals 406 to the beam steering device 202 that selectively steers the one or more optical power signals 406 as the one or more steered optical power signals 408. The one or more steered optical power signals 408 are transmitted transdermally through the living subject 103 and received by the optical-electrical converter 418 that converts the received one or more steered optical power signals 408 to the one or more electrical power signals 420 that powers the control circuitry 422 for directing the operation of the at least one external device 416.

Although the illustrated embodiment of the system 400 employs the beam steering device 202, in other embodiments, the beam steering device 202 may be omitted. In such an embodiment, a user may control the transdermal transmission of the one or more optical power signals 406 responsive to the user inputting user input into the user interface 424 of the at least one external device 416.

Figure 5:
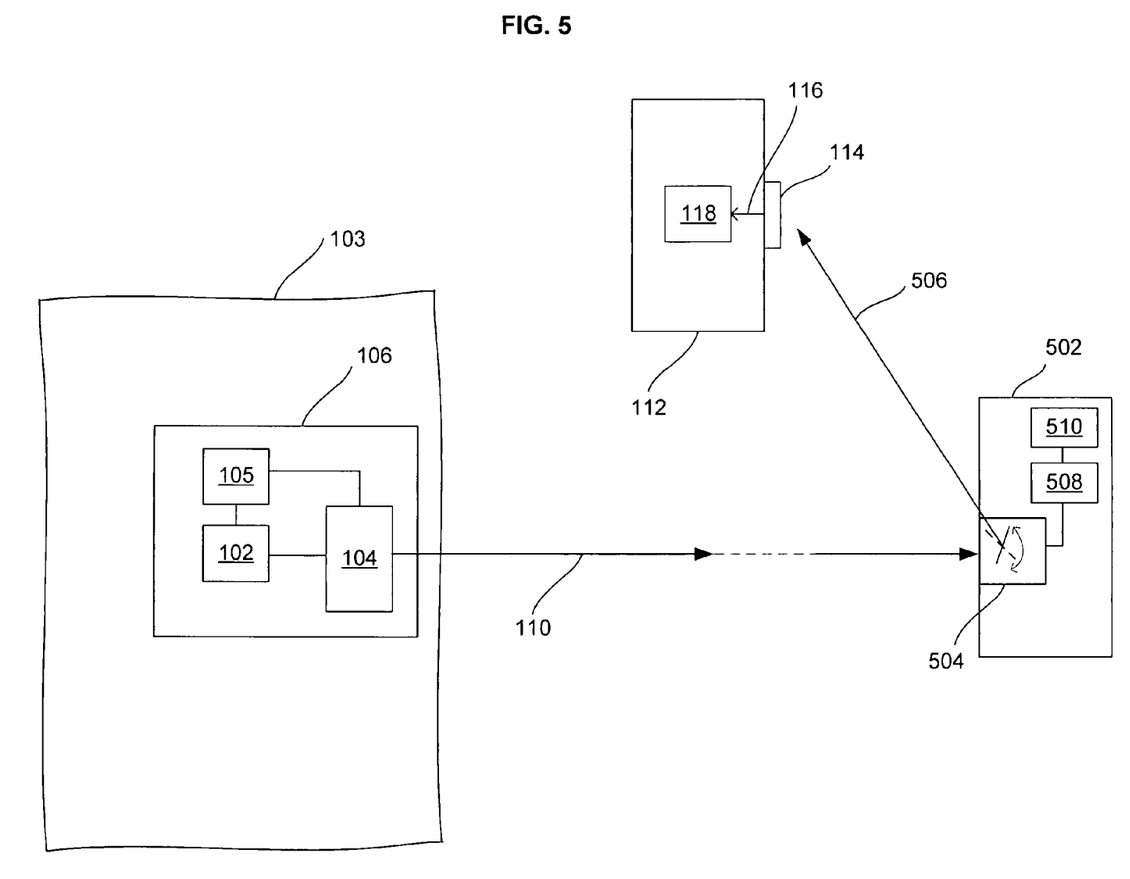
FIG. 5 is a functional block diagram of an embodiment of a system configured to transmit one or more optical power signals transdermally out of a living subject to a beam steering apparatus that directs the one or more optical power signals to at least one external device.

FIG. 5 is a functional block diagram of an embodiment of a system 500 configured to transmit one or more optical power signals transdermally out of a living subject to a beam steering apparatus that directs the one or more optical power signals to at least one external device. The system 500 differs from the system 100 shown in FIG. 1 in that an external beam steering apparatus 502 (i.e., a target) is provided, which is configured to selectively direct the one or more optical power signals 110 transmitted transdermally out of the living subject 103. The beam steering apparatus 502 may include a beam steering device 504, such as at least one of a diffraction grating, a micro-electro-mechanical scanner, an acoustic-optical device, or an electro-optical device configured to selectively steer the one or more optical power signals 110 as one or more steered optical power signals 506. The one or more steered optical power signals 506 may be directed to the optical-electrical converter 114 of the at least one external device 112, which converts the one or more steered optical power signals 506 to electricity to power the at least one external device 112. The beam steering apparatus 502 may also include control circuitry 508 operably coupled to the beam steering device 504 and an associated user interface 510 that enables a user to program or control, for example, the direction that the one or more optical power signals 110 are steered.

In an embodiment, the beam steering apparatus 502 may be replaced with an optical-optical converter configured to alter a peak wavelength of the one or more optical power signals 110 (e.g., an up-converting or down-converting optical device or material). In an embodiment, the beam steering apparatus 502 may be replaced with an optical-thermal converter configured to convert the one or more optical power signals 110 to heat. For example, the optical-thermal converter may include a body of material selected to substantially absorb the one or more optical power signals 110. In an embodiment, the optical-optical converter may be included in the beam steering apparatus 502 and positioned to alter a peak wavelength of the one or more steered optical power signals 506. In an embodiment, focusing optics may be disposed in the optical path of the one or more optical power signals 110 or the one or more steered optical power signals 506.

Figure 6:
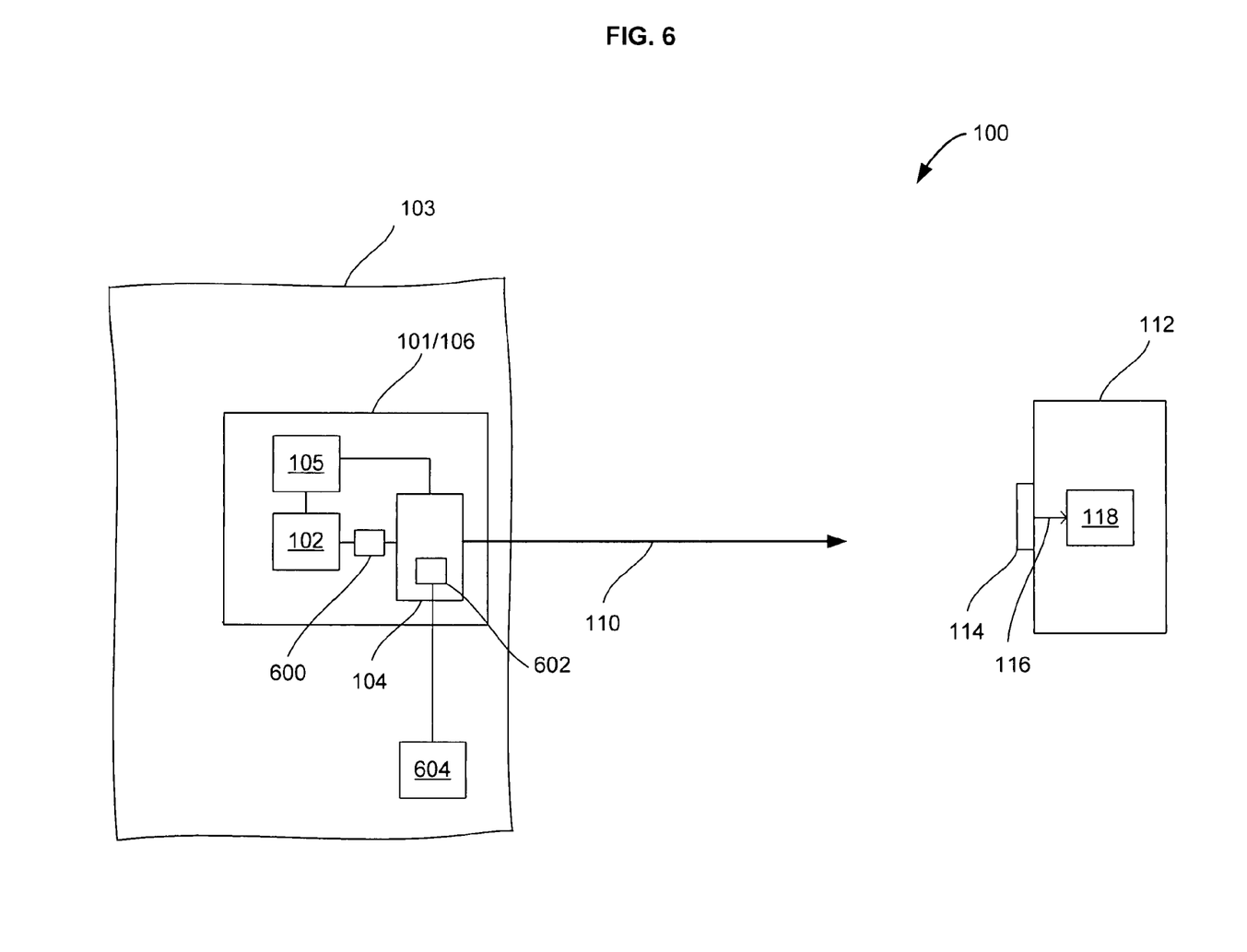
FIG. 6 is functional block diagram of an embodiment of the system shown in FIG. 1 that includes a power converter operably coupled to the electrical-optical converter or at least one power input integrated with the electrical-optical converter configured for receiving power from one or more additional power sources.

Referring to FIG. 6, in any of the above-described embodiments, electrical energy provided by a power source may be converted to a different electrical state. For example, in the system 100 shown in FIG. 6, a power converter 600 may be electrically coupled to the power source 102 and the electrical-optical converter 104. The power converter 600 is configured to convert electrical energy provided by the power source 102 to a different electrical state prior to being received by the electrical-optical converter 104. For example, the power converter 600 may be configured to convert a direct current electrical signal to an alternating current electrical signal (i.e., an inverter), configured to converter a direct current waveform to a selected different direct current waveform, or other suitable treatment that may be better used by the electrical-optical converter 104.

In some embodiments, the electrical-optical converter 104 may include one or more power inputs 602 configured to receive power from one or more additional power sources 604 that are independent from the power source 102. For example, the one or more power sources 604 may include at least one of a battery, an ultrasonic power source, an inductive power source, or an optical power source. When the one or more power sources 604 include an ultrasonic power source, an inductive power source, or an optical power source, an ultrasonic-electrical converter, inductive receiver, or optical-electrical converter may be provided, respectively, to convert the type of energy to electrical energy useable by the electrical-optical converter 104. In some embodiments, the control circuitry 105 may be configured to instruct the electrical-optical converter to selectively extract power from the power source 102 or the one or more power sources 604. For example, when one of the power sources exhibits a power level below a threshold power level, the control circuitry 105 may instruct the electrical-optical converter 104 to selectively extract power from one of the power sources having sufficient power.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

The invention claimed is:

1. A method, comprising:
converting electrical energy within a living subject into one or more optical power signals;
receiving the one or more optical power signals at a beam steering device disposed in a housing;
selectively modifying one or more optical parameters of the one or more optical power signals with the beam steering device; and
transmitting the one or more optical power signals transdermally out of the living subject after the modifying.

2. The method of claim 1, wherein transmitting the one or more optical power signals transdermally out of the living subject after the optical processing includes transmitting the one or more optical power signals with a power of at least about 10 µW.

3. The method of claim 2, wherein the power is about 10 µW to about 10 W.

4. The method of claim 2, wherein the power is about 10 µW to about 1 mW.

5. The method of claim 2, wherein the power is about 1 mW to about 100 mW.

6. The method of claim 2, wherein the power is about 100 mW to about 1 W.

7. The method of claim 1, further comprising generating the electrical energy from internal body energy of the living subject.

8. The method of claim 7, wherein generating the electrical energy from internal body energy of the living subject includes converting at least one of muscular energy, fluid energy, acceleration energy, or thermal energy into the electrical energy.

9. The method of claim 1, further comprising receiving the electrical energy from an energy storage device.

10. The method of claim 9, wherein the energy storage device includes a battery or a capacitive device.

11. The method of claim 9, wherein selectively modifying one or more optical parameters of the one or more optical power signals includes focusing the one or more optical power signals prior to being transmitted transdermally out of the living subject.

12. The method of claim 1, wherein transmitting the one or more optical power signals transdermally out of the living subject after the modifying includes transmitting the one or more optical power signals to a target located externally to the living subject.

13. The method of claim 1, further comprising converting the one or more transmitted optical power signals into one or more electrical power signals.

14. The method of claim 13, further comprising powering at least one device located externally to the living subject using the one or more electrical power signals.

15. The method of claim 14, wherein powering at least one device using the one or more electrical power signals includes powering a personal electronic device located externally to the living subject.

16. The method of claim 1, further comprising transmitting the one or more optical power signals responsive to receiving instructions transmitted transdermally into the living subject from at least one device located externally to the living subject.

17. The method of claim 1, wherein selectively modifying one or more optical parameters of the one or more optical power signals includes at least partially countering optical spreading that occurs as the one or more optical power signals pass through tissue of the living subject by focusing the one or more optical power signals prior to being transmitted transdermally out of the living subject.

18. The method of claim 1, wherein selectively modifying one or more optical parameters of the one or more optical power signals includes partially confining the one or more optical power signals to a receiving aperture by focusing the one or more optical power signals prior to being transmitted transdermally out of the living subject.

19. The method of claim 1, wherein selectively modifying one or more optical parameters of the one or more optical power signals includes steering the one or more optical power signals prior to being transmitted transdermally out of the living subject.

20. The method of claim 1, wherein selectively modifying one or more optical parameters of the one or more optical power signals includes at least partially directing the one or more optical power signals to a target located externally to the living subject by steering the one or more optical power signals prior to being transmitted transdermally out of the living subject.

21. The method of claim 1, further comprising selectively providing the electrical energy from one of first or second power sources.

22. The method of claim 1, further comprising modifying the electrical energy prior to the converting.

23. A method, comprising:
converting electrical energy within a living subject into one or more optical power signals;
receiving the one or more optical power signals at a beam steering device disposed in a housing;
modifying one or more optical parameters of the one or more optical power signals with the beam steering device;
transmitting the one or more optical power signals transdermally out of the living subject after the modifying;
converting the one or more transmitted optical power signals into one or more electrical power signals; and
powering at least one device located externally to the living subject using the one or more electrical power signals.

24. The method of claim 23, further comprising generating the electrical energy, with an electrical generator disposed within a living subject, by converting internal body energy of the living subject to the electrical energy.

25. The method of claim 23, further comprising utilizing the powering to control an operation of the at least one device.

26. A method, comprising:
generating electrical energy, with an electrical generator disposed within a living subject, by converting internal body energy of the living subject to the electrical energy
converting the electrical energy within the living subject into one or more optical power signals;
receiving the one or more optical power signals at a beam steering device disposed in a housing;
modifying one or more optical parameters of the one or more optical power signals with the beam steering device;
transmitting the one or more optical power signals transdermally out of the living subject after the modifying;

converting the one or more transmitted optical power signals into one or more electrical power signals;

powering at least one device located externally to the living subject using the one or more electrical power signals; and utilizing the powering to control an operation of the at least one device.

* * * * *